United States Patent
Nitta et al.

(10) Patent No.: US 10,646,186 B2
(45) Date of Patent: May 12, 2020

(54) X-RAY CT APPARATUS, INFORMATION PROCESSING DEVICE AND INFORMATION PROCESSING METHOD

(71) Applicant: Toshiba Medical Systems Corporation, Otawara-shi (JP)

(72) Inventors: Shuhei Nitta, Ota (JP); Toshiyuki Ono, Kawasaki (JP); Takashi Ida, Kawasaki (JP); Hiroaki Nakai, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 659 days.

(21) Appl. No.: 15/408,899

(22) Filed: Jan. 18, 2017

(65) Prior Publication Data

US 2017/0202531 A1    Jul. 20, 2017

(30) Foreign Application Priority Data

Jan. 18, 2016  (JP) ................................ 2016-007327
Jan. 17, 2017  (JP) ................................ 2017-006194

(51) Int. Cl.
*A61B 6/00*  (2006.01)
*A61B 6/06*  (2006.01)

(52) U.S. Cl.
CPC .............. *A61B 6/5211* (2013.01); *A61B 6/06* (2013.01); *A61B 6/4241* (2013.01); *A61B 6/482* (2013.01); *A61B 6/50* (2013.01)

(58) Field of Classification Search
CPC ........ A61B 6/032; A61B 6/482; A61B 6/5205
See application file for complete search history.

(56) References Cited

U.S. PATENT DOCUMENTS

| 7,372,934 B2 | 5/2008 | De Man et al. | |
|---|---|---|---|
| 2017/0186195 A1* | 6/2017 | Lin | ........................ G06T 11/008 |

FOREIGN PATENT DOCUMENTS

| JP | 5-161633 | 6/1993 |
|---|---|---|
| JP | 2007-167663 | 7/2007 |

* cited by examiner

*Primary Examiner* — Dani Fox
(74) *Attorney, Agent, or Firm* — Oblon, McClelland, Maier & Neustadt, L.L.P.

(57) ABSTRACT

An X-ray computed tomography (CT) apparatus according to an embodiment includes an X-ray generator, an X-ray detector and processing circuitry. The X-ray generator irradiates X-rays to a subject. The X-ray detector detects the X-rays that have passed through the subject. The processing circuitry calculates an estimated spectrum based on an irradiation spectrum, an estimated length and information indicating a distortion of a spectrum occurring in a path of the X-rays passing through the subject, the estimated length representing an estimated value of an X-ray transmission length of a material of decomposition target. The processing circuitry determines an X-ray transmission length of the material of decomposition target based on the estimated spectrum and a detected spectrum that is a spectrum after the X-rays have passed through the subject and that is detected by the X-ray detector.

16 Claims, 6 Drawing Sheets

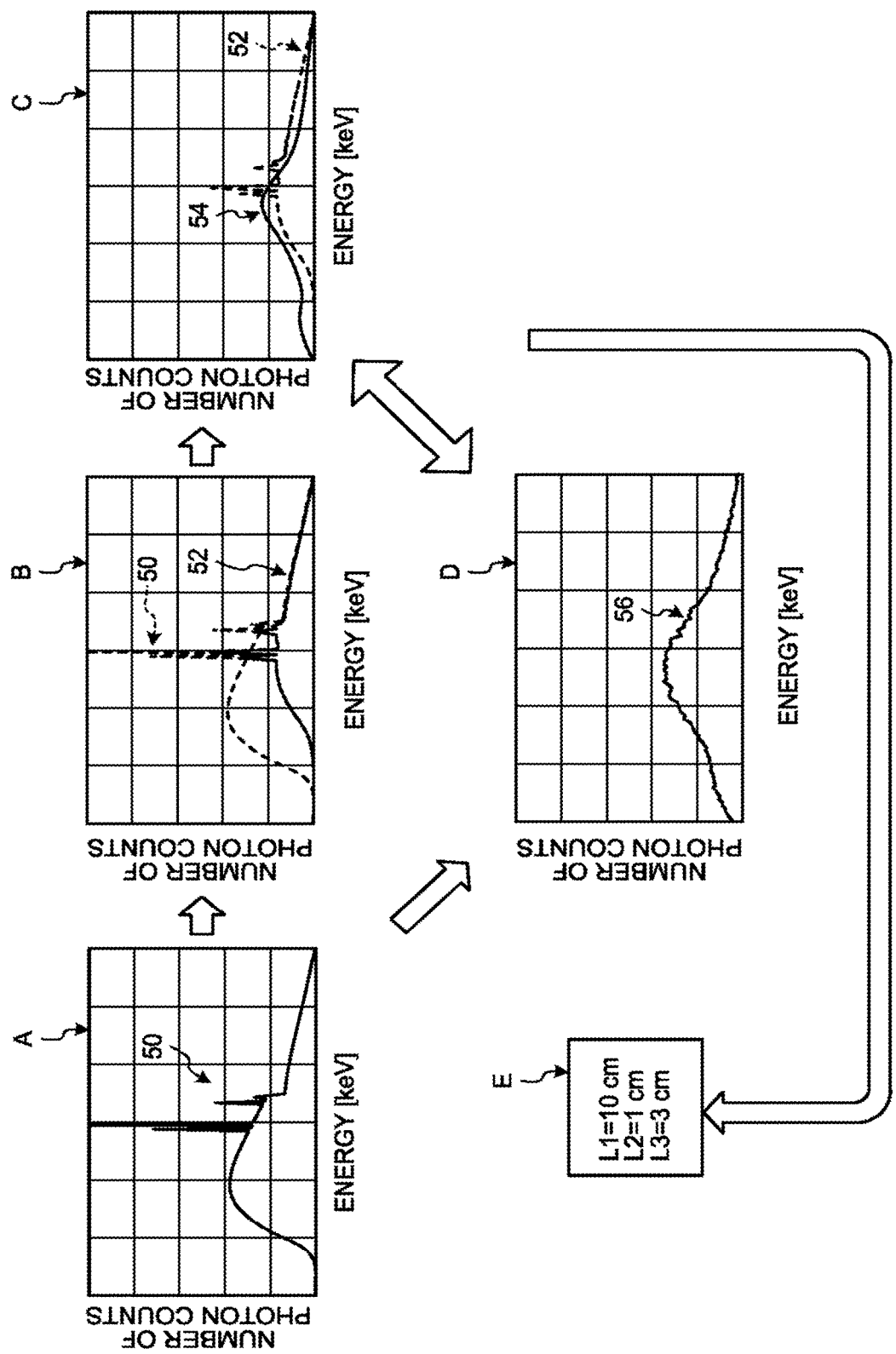

US 10,646,186 B2

X-RAY CT APPARATUS, INFORMATION PROCESSING DEVICE AND INFORMATION PROCESSING METHOD

CROSS-REFERENCE TO RELATED APPLICATIONS

This application is based upon and claims the benefit of priority from Japanese Patent Application No. 2016-007327, filed on Jan. 18, 2016; and Japanese Patent Application No. 2017-006194, filed on Jan. 17, 2017, the entire contents of all of which are incorporated herein by reference.

FIELD

Embodiments described herein relate generally to an X-ray computed tomography (CT) apparatus, an information processing device, and an information processing method.

BACKGROUND

As a practical application of X-ray CT, there is a technique that estimates the type, an atomic number, the density, and the like of a material in a subject, which technique is known as material decomposition. In material decomposition, the fact that the interaction between the X-ray and the materials are different depending on the energy of the X-rays is used.

As a technology performing material decomposition, there is known a technology that utilizes a spectrum obtained by measuring each energy of photons that have passed through the subject and that have reached the detector. For example, there is disclosed a technique in which abundance of a material is calculated based on the average absorption coefficient of the material and an image obtained by irradiating to the subject radioactive rays of a plurality of energies.

However, in the prior art, the spectrum and the image used for the material decomposition are sometimes different from the actual spectrum of the radiation that has been transmitted through the subject or the image obtained from the spectrum. Thus, in the conventional technique in which material decomposition is performed based on the spectrum and the image, it was difficult to accurately perform material decomposition.

BRIEF DESCRIPTION OF THE DRAWINGS

FIG. 3 is a diagram schematically illustrating processing executed by processing circuitry;

DETAILED DESCRIPTION

Figure 1:
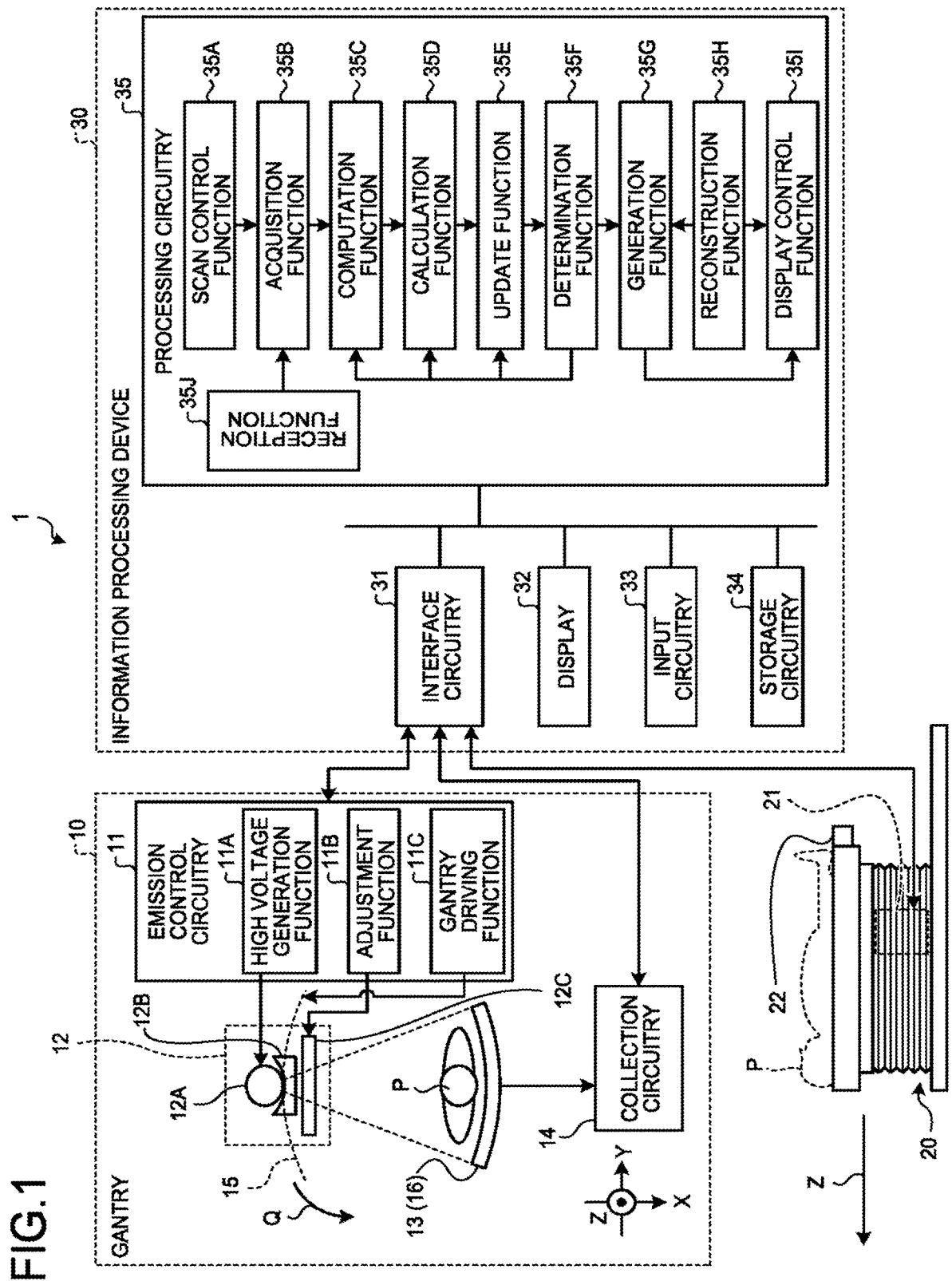
FIG. 1 is a diagram illustrating an example of an X-ray computed tomography (CT) apparatus according to an embodiment.

An X-ray computed tomography (CT) apparatus according to an embodiment includes an X-ray generator, an X-ray detector and processing circuitry. The X-ray generator irradiates X-rays to a subject. The X-ray detector detects the X-rays that have passed through the subject. The processing circuitry calculates an estimated spectrum based on an irradiation spectrum, an estimated length and information indicating a distortion of a spectrum occurring in a path of the X-rays passing through the subject, the estimated spectrum being estimated as a spectrum after the X-rays have passed through the subject, the irradiation spectrum being a spectrum before reaching the subject among spectra indicating a distribution of number of photon counts for each energy of the X-rays, the estimated length representing an estimated value of an X-ray transmission length of a material of decomposition target. The proccing circuitry determines an X-ray transmission length of the material of decomposition target based on the estimated spectrum and a detected spectrum that is a spectrum after the X-rays have passed through the subject and that is detected by the X-ray detector.

An X-ray CT apparatus, an information processing device, and an information processing method according to the embodiment are described in detail below with reference to the drawings. In the embodiment, components denoted with the same reference numeral are regarded as components that perform the same operations, and redundant description thereof will be omitted as appropriate.

FIG. 1 is a diagram illustrating an example of an X-ray CT apparatus 1 according to the present embodiment.

The X-ray CT apparatus 1 irradiates X-rays that is an example of radioactive rays, to a subject P. Examples of the X-ray CT apparatus 1 include a spectral CT apparatus and a photon counting CT apparatus that obtain a cross-sectional image of a subject P.

The X-ray CT apparatus 1 includes a gantry 10, a couch device 20, and an information processing device 30. The gantry 10 and the couch device 20 are connected to the information processing device 30 in such a manner as to be capable of sending and receiving data and signals to and from the information processing device 30.

The gantry 10 irradiates X-rays to the subject P, and collects spectrum information on the X-rays that have passed through the subject P. The gantry 10 includes emission control circuitry 11, an X-ray generator 12, a rotation frame 15, a detector 13, and collection circuitry 14.

The X-ray generator 12 generates the X-rays, and irradiates the X-rays to the subject P. The X-ray generator 12 includes an X-ray tube 12A, a wedge 12B, and a collimator 12C.

The X-ray tube 12A is a vacuum tube that generates X-rays in accordance with voltage supplied from the emission control circuitry 11. The X-ray tube 12A irradiates the X-rays thus generated onto the subject P. For example, the X-ray tube 12A generates X-rays in a form of a beam extending in a conical or pyramid shape.

The wedge 12B is a filter for adjusting an amount of X-rays irradiated from the X-ray tube 12A. The collimator 12C is a slit for adjusting an irradiation range of the X-rays the amount of which has been adjusted by the wedge 12B.

Thus, the spectrum of the X-rays irradiated to the subject P from the X-ray generator 12 is determined based on: high voltage and current supplied to the X-ray tube 12A; the type of a target (for example, tungsten and the like) used for a radiation source; a target angle; the type (for example, beryllium and the like) and a thickness of a filter; the type and a thickness of the wedge 12B; and the like.

The rotation frame 15 is a ring-shaped supporting member. The X-ray generator 12 and the detector 13 are supported by the rotation frame 15 opposing each other with the subject P in between. The subject P is positioned at the center of a circle defined by the rotation frame 15. The rotation frame 15 is rotatable around the subject P. Thus, the X-ray generator 12 and the detector 13 are rotatable around the subject P, while remaining opposing each other.

The detector 13 detects the spectrum of the X-rays that have been irradiated from the X-ray tube 12A and transmitted through the subject P. In other words, the detector 13 detects the spectrum indicating the number of photon counts of the X-rays that have transmitted through the subject P, for each energy.

In the present embodiment, the spectrum detected by the detector 13 is referred to as a detected spectrum. The detected spectrum is described in detail later.

The detector 13 detects the detected spectrum for each position of the X-ray generator 12, while rotating along the circumference direction of the rotation frame 15. The position of the X-ray generator 12 is a relative position of the X-ray generator 12 (the X-ray tube 12A to be more specific) with respect to the subject P. The position of the X-ray generator 12 is referred to as "view" in some cases. For example, the position of the X-ray generator 12 is represented by an angle relative to a predetermined position defined as 0° in a 360° circle along the circumference direction of the rotation frame 15. For example, it is assumed that the gantry 10 detects the spectra for every 0.5° degrees. In this case, the position of the X-ray generator 12 can be represented by an angle for every 0.5° degrees.

The detector 13 includes a plurality of detection elements 16. The detection element 16 outputs a signal corresponding to the incident X-rays. For example, the detection element 16 is a cadmium telluride (CdTe)-based semiconductor device.

In the present embodiment, the detectors 13 are two-dimensionally arranged in the circumference direction of the rotation frame 15 (see a direction indicated by an arrow Q in FIG. 1) and in an orthogonal direction orthogonal to the circumference direction (see a direction indicated by an arrow Z in FIG. 1) on a facing surface facing the X-ray generator 12.

In the present embodiment, the detection element 16 outputs a pulsed signal to the collection circuitry 14 every time a single photon of the X-rays enters. With the pulse signal, the energy of the incident photon and the number of incident photons can be measured.

The detector 13 may be one of a direct conversion type or an indirect conversion type. The detector 13 of the direct conversion type directly converts the photon entering the detection element 16 into an electrical signal. The detector 13 of the indirect conversion type includes a scintillator disposed on an X-ray incident side of the detection element 16.

The emission control circuitry 11 controls operations of the X-ray generator 12 and the rotation frame 15. The emission control circuitry 11 has a high voltage generation function 11A, an adjustment function 11B, and a gantry driving function 11C.

Various processing functions implemented with the high voltage generation function 11A, the adjustment function 11B, and the gantry driving function 11C are in a form of computer-executable programs and are stored in storage circuitry. The emission control circuitry 11 is a processor that reads the programs from the storage circuitry, and executes the programs to implement the functions corresponding to the programs. In other words, the emission control circuitry 11 in the state of having loaded the programs has the functions illustrated in the emission control circuitry 11 illustrated in FIG. 1.

In the description with reference to FIG. 1, the processing functions executed in the high voltage generation function 11A, the adjustment function 11B, and the gantry driving function 11C are realized with the emission control circuitry 11 as a single circuitry. Alternatively, the emission control circuitry 11 may include a combination of a plurality of independent processors, and the functions may be realized by the processors executing the programs.

The high voltage generation function 11A generates high voltage, and supplies the high voltage thus generated to the X-ray tube 12A. The adjustment function 11B adjusts the aperture and the position of the collimator 12C. The adjustment of the aperture and the position of the collimator 12C is directly related to the adjustment of the irradiation range of the X-ray irradiated on the subject P from the X-ray tube 12A. For example, the adjustment function 11B adjusts the aperture of the collimator 12C to adjust the irradiation range of the X-rays, that is, a fan angle or a cone angle of the X-rays.

The gantry driving function 11C performs control such that the rotation frame 15 is rotated. The control performed by the gantry driving function 11C causes the rotation frame 15 to rotate in a circular path around the subject P. Thus, the X-ray generator 12 and the detector 13 rotate around the subject P, in accordance with the rotation of the rotation frame 15, while remaining opposite to each other with the subject P in between by the rotation frame 15.

The gantry 10 is not limited to the configuration of rotating the X-ray generator 12 and the detector 13.

For example, the gantry 10 may have a configuration of rotating only the X-ray generator. In such a configuration, the detector 13 may have a configuration including the detection elements 16 arranged over the entire length of the rotation frame 15 in the circumference direction. The rotation frame 15 may have a configuration of supporting the X-ray generator 12.

The collection circuitry 14 uses the signals received from the plurality of detection elements 16 of the detector 13 to count the number of photons of the X-rays entering the detection elements 16. The collection circuitry 14 executes calculation processing based on a pulse-signal waveform indicated by the signals received from the plurality of detection elements 16. The collection circuitry 14 executes the calculation processing to measure the energy of the photon that has triggered the signal output, for each of the plurality of detection elements 16.

Through the processing described above, the collection circuitry 14 collects the detected spectrum indicating the number of photon counts with respect to the energy of the X-rays from each of the detection elements 16, and outputs the detected spectrum to the information processing device 30. Thus, the detected spectrum detected by the detector 13 is, to say in more detail, a spectrum obtained by collecting the signals output from the detection elements 16 by the collection circuitry 14.

As described above, the X-ray generator 12 irradiates the X-rays to the subject P from a plurality of different positions by rotating around the subject P. Thus, in the present embodiment, the collection circuitry 14 receives the signal from each of the plurality of detection elements 16 of the detector 13 for each position of the X-ray generator 12.

The collection circuitry 14 collects the number of photon counts with respect to the energy of the X-rays, for each position of the X-ray generator 12 and for each detection element 16. The collection circuitry 14 outputs the number of photon counts with respect to the energy of the X-rays to the information processing device 30, for each position of the X-ray generator 12 and for each detection element 16. In this process, the collection circuitry 14 outputs collection information to the information processing device 30. The collection information includes the position of the X-ray generator 12, identification information on the detection element 16, and the corresponding detected spectrum.

In the example described in the present embodiment, the position of the detection element 16 in the detector 13 is used as the identification information on the detection element 16. Thus, in the description below, the identification information on the detection element 16 may be also referred to as the position of the detection element 16.

The subject P is placed on the couch device 20 including a couch driving device 21 and a couchtop 22.

The couchtop 22 is a couch such as a bed on which the subject P lays down. The couchtop 22 is movable in a direction of a body axis direction (see a direction indicated by an arrow Z in FIG. 1) of the subject P laying on the couchtop 22. The couch driving device 21 moves the couchtop 22 in the body axis direction of the subject P, under control by the information processing device 30. In the present embodiment described herein, the body axis direction of the subject P matches the rotational direction of the rotation frame 15. When the couchtop 22 moves in the body axis direction of the subject P, the subject P, laying on the couchtop 22, is conveyed to move into and out from the inner side of the rotation frame 15.

The information processing device 30 controls the gantry 10 and the couch device 20.

The information processing device 30 includes interface circuitry 31, a display 32, input circuitry 33, storage circuitry 34, and processing circuitry 35.

The interface circuitry 31 communicates with each of the gantry 10 and the couch device 20.

The input circuitry 33 receives various operation instructions from the user. The input circuitry 33 outputs an instruction signal, corresponding to the received operation instruction, to the processing circuitry 35. For example, the input circuitry 33 is a mouse, a keyboard, a button, a trackball, a joystick, or the like.

The display 32 displays various images. For example, the display 32 displays a display image (described later in detail), a CT image (described later in detail), and the like.

For example, the display 32 is a cathode ray tube (CRT) display, a liquid crystal display (LCD), an organic electroluminescence (EL), or the like.

The storage circuitry 34 stores various types of data. For example, the storage circuitry 34 is a hard disk drive (HDD), a solid-state drive (SSD), a random-access memory (RAM), a semiconductor memory device such as a flash memory, an optical disk, or the like.

The processing circuitry 35 controls the gantry 10 and the couch device 20, and executes information processing with various types of data acquired from the gantry 10.

The processing circuitry 35 has a scan control function 35A, an acquisition function 35B, a computation function 35C, a calculation function 35D, an update function 35E, a determination function 35F, a generation function 35G, a reconstruction function 35H, a display control function 35I, and a reception function 35J.

For example, the scan control function 35A, the acquisition function 35B, the computation function 35C, the calculation function 35D, the update function 35E, the determination function 35F, the generation function 35G, the reconstruction function 35H, the display control function 35I, and the reception function 35J may be partially or entirely implemented by electronic circuitry such as a central processing unit (CPU) executing a computer program, that is, by software.

For example, processing functions implemented with the scan control function 35A, the acquisition function 35B, the computation function 35C, the calculation function 35D, the update function 35E, the determination function 35F, the generation function 35G, the reconstruction function 35H, the display control function 35I, and the reception function 35J are in a form of computer-executable programs and are stored in the storage circuitry 34.

The information processing device 30 is a processor that reads out the programs from the storage circuitry 34 and executes the programs to implement the functions corresponding to the programs. In other words, the processing circuitry 35 in a state of having loaded the programs has the functions illustrated in the processing circuitry 35 in FIG. 1.

In the description with reference to FIG. 1, the processing functions executed with the scan control function 35A, the acquisition function 35B, the computation function 35C, the calculation function 35D, the update function 35E, the determination function 35F, the generation function 35G, the reconstruction function 35H, the display control function 35I, and the reception function 35J are implemented by the processing circuitry 35 as a single unit. Alternatively, the processing circuitry 35 may include a combination of a plurality of independent processors, and the functions may be implemented by the processors executing the programs.

The scan control function 35A, the acquisition function 35B, the computation function 35C, the calculation function 35D, the update function 35E, the determination function 35F, the generation function 35G, the reconstruction function 35H, the display control function 35I, and the reception function 35J may be partially or entirely implemented by hardware, or by a combination of software and hardware.

The hardware implementing the functions may include electronic circuitry such as an integrated circuit (IC), an application specific integrated circuit (ASIC), and a field programmable gate array (FPGA).

The scan control function 35A controls the emission control circuitry 11, the collection circuitry 14, and the couch driving device 21. More specifically, the scan control function 35A controls the emission control circuitry 11 such that the rotation frame 15 rotates, the X-ray tube 12A irradiates the X-rays to the subject P, and the aperture and the position of the collimator 12C are adjusted. With this control, the gantry 10 continuously or intermittently irradiates the X-rays to the subject P from the X-ray generator 12, while rotating the rotation frame 15.

For example, the scan control function 35A controls the gantry 10 such that helical scan or non-helical scan is executed.

The scan control function 35A receives the collection information from the collection circuitry 14 and stores the collection information in the storage circuitry 34. As described above, the collection information includes the position of the X-ray generator 12, the position of the detection element 16, and the corresponding detected spectrum.

Now, the spectra will be described. FIG. 2A to FIG. 2D are diagrams illustrating examples of the spectra.

The X-rays irradiated from the X-ray generator 12 pass through the subject P and reach the detector 13 and are detected by the detector 13.

Figure 2A:
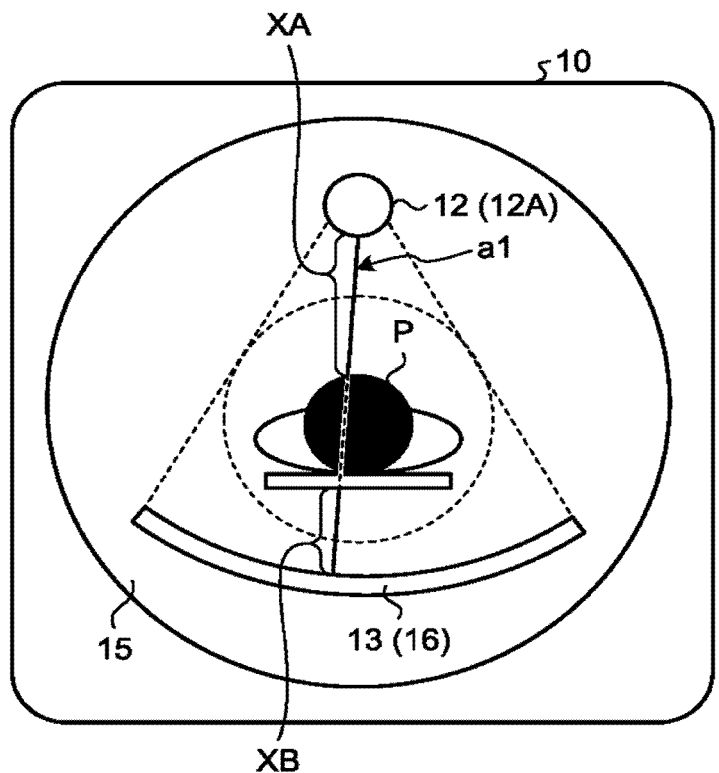
FIG. 2A to FIG. 2D are diagrams illustrating examples of a spectrum.

The spectrum of the X-rays irradiated from the X-ray tube 12A and reach the subject P are referred to as an irradiation spectrum 50. FIG. 2A illustrates an example where an X-ray al is irradiated from the X-ray generator 12 to the detection element 16. In this case, the irradiation spectrum 50 is a spectrum of the X-ray, as the X-ray a1, in an area XA (see FIG. 2B). The area XA is an air area where the attenuation of the X-ray can be ignored.

The irradiation spectrum 50 is determined based on the high voltage and current supplied to the X-ray tube 12A, the type of the target (for example, tungsten and the like) used for the radiation source, and the type and the thickness of the wedge 12B. Thus, the irradiation spectrum 50 can be obtained from accurate actual measurement or highly accurate simulation. Thus, in the present embodiment, the irradiation spectrum 50 is stored in advance in the storage circuitry 34.

In the present embodiment, the spectrum of the X-ray after passing through the subject P and before reaching the detection element 16 is referred to as a transmission spectrum 52. For example, as illustrated in FIG. 2A, the transmission spectrum 52 corresponds to the spectrum of the X-ray, as the X-ray a1 irradiated from the X-ray generator 12 to the detection element 16, in an area XB (see FIG. 2C).

The irradiation spectrum 50 of the X-rays irradiated from the X-ray tube 12A to the subject P attenuates while the X-rays pass through the subject P. The attenuation depends on materials in the subject P. Thus, the transmission spectrum 52, as the spectrum of the X-rays that have passed through the subject P, corresponds to a shape of the spectrum including the attenuation depending on the material in the subject P. More specifically, the transmission spectrum 52 is determined based on the composition of the material in a path through which the X-rays have passed through the subject P and the irradiation spectrum 50 of the X-rays irradiated to the subject P.

In the present embodiment, the spectrum of the X-rays detected by the detector 13 is referred to as a detected spectrum 54. More specifically, the detected spectrum 54 corresponds to the spectrum of the X-rays detected by the detector 13 (see FIG. 2D).

Ideally, the transmission spectrum 52 should be the same as the detected spectrum 54. However, typically, the detected spectrum 54 as the actually measured spectrum is different from the transmission spectrum 52 corresponding to the X-rays immediately before reaching the detector 13, due to the detector response or the like of the detector 13 in an actual operation.

Figure 2B:
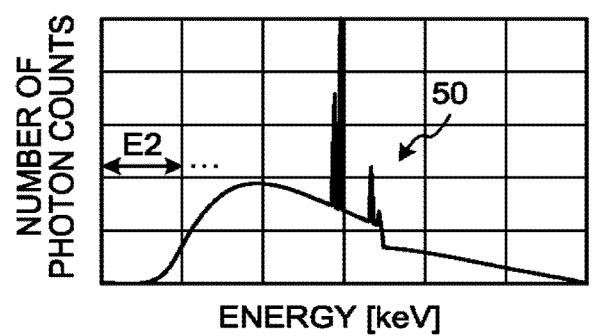
Figure 2C:
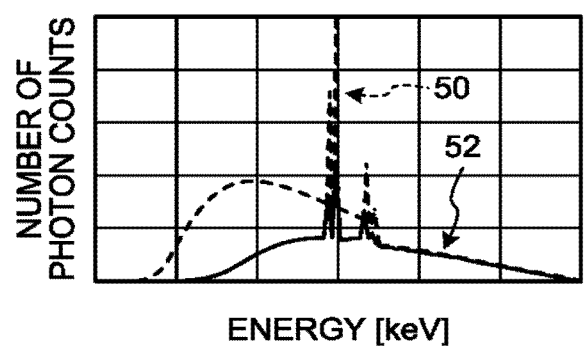
Figure 2D:
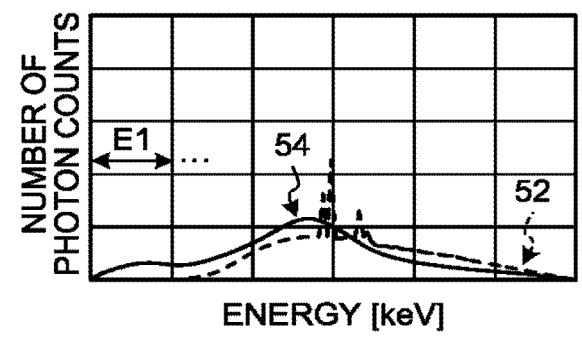

The shapes of the spectra (the irradiation spectrum 50, the transmission spectrum 52, and the detected spectrum 54) illustrated in FIG. 2B to FIG. 2D are merely an example, and the shape is not limited to these.

The irradiation spectrum 50 and the detected spectrum 54 are defined by the following formulae (Formula (1) and Formula (2)).

$$s_0(c,e) \quad (1)$$

$$s_1(c,v,e) \quad (2)$$

In the present embodiment, the irradiation spectrum 50 is defined by Formula (1) described above. In Formula (1), c represents the position of the detection element 16 and e represents the energy (keV) of the X-ray.

In Formula (1), $S_0(c,e)$ represents the irradiation spectrum 50, that is, a group of numbers of photon counts corresponding to energies e of the X-rays irradiated on the detection element 16 at the position c. More specifically, $S_0(c,e)$ represents a group of estimated values of the number of photon counts of the X-rays expected to be irradiated on the detection element 16 at the position c with the energy e, assuming that there is no subject P. In other words, for example, the irradiation spectrum 50 is an X-ray spectrum indicating the distribution of the numbers of photon counts with respect to the energies e of the X-rays finally detected by the detection element 16 at the position c, and is an X-ray spectrum of the X-rays after being irradiated from the X-ray generator 12 and before reaching the subject P in a path connecting between the X-ray generator 12 and the detection element 16 at the position c. Formula (1) includes no parameter indicating the position of the X-ray generator 12. This is because the irradiation spectrum 50 does not change in accordance with the position of the X-ray generator 12. However, Formula (1) may further include the parameter indicating the position of the X-ray generator 12. An example of the irradiation spectrum 50 is not limited to the example described above. The irradiation spectrum 50 may not include the position c of the detection element 16 as an argument, and thus may be represented by $S_0(e)$. Furthermore, one example of the irradiation spectrum 50 may include the irradiation spectrum 50 that is integrated for the energy e of the X-ray to be represented by $S_0$.

In the present embodiment, the detected spectrum 54 is defined by Formula (2) described above. In Formula (2), c represents the position of the detection element 16, e represents the energy (keV) of the X-rays, v represents the position of the X-ray generator 12, and $S_1(c,v,e)$ represents the detected spectrum 54. More specifically, $S_1(c,v,e)$ represents the group of the numbers of photon counts corresponding to energies e of the X-ray detected by the detection element 16 at the position c when the X-ray generator 12 is at the position v.

More detailed description will be given on e in Formulae (1) and (2). In the present embodiment, each of the irradiation spectrum 50 and the detected spectrum 54 indicates the number of counted photons for each energy band (hereinafter, also simply referred to as energy) with a predetermined energy width.

The energy width of the energy band corresponding to each of the numbers of photon counts indicated by the detected spectrum 54 is referred to as a first energy width E1 (see FIG. 2D).

The energy width of the energy band corresponding to each of the numbers of photon counts indicated by the irradiation spectrum 50 is referred to as second energy width E2 (see FIG. 2B).

In the second energy width E2 is equal to or smaller than the first energy width E1.

The detected spectrum 54 indicates the number of photon counts in each of the energy bands with the first energy width E1 between 0 keV and the maximum energy. For example, a maximum value of the energy with the largest possible number photons detectable by the detector 13 may be set as the maximum energy.

The irradiation spectrum 50 indicates the number of photon counts in each of the energy bands with the second energy width E2 between 0 keV and the maximum energy described above.

The energy bands may or may not at least partially overlap one another.

Values of the first energy width E1 and the second energy width E2 are not particularly limited, but are preferably smaller than 20 keV, and are more preferably not larger than 1 keV.

In the example described in the present embodiment, the first energy width E1 and the second energy width E2 are each 1 keV.

Thus, in the present embodiment, the irradiation spectrum 50 and the detected spectrum 54 each indicates the number of photon counts corresponding to the energy band of each of the energy widths that is 1 keV.

In the present embodiment, e of Formulae (1) and (2) means to show the upper limit value of the energy indicated by the energy band of a corresponding energy width. More specifically, in the description of the present embodiment, e=1 represents the energy band in a range between 0 keV inclusive and 1 keV exclusive, and e=2 represents the energy band in a range between 1 keV inclusive and 2 keV inclusive. Similarly, e=100 represents the energy band in a range between 99 keV inclusive and 100 keV inclusive.

Next, the distortion and attenuation of the spectrum occurring in the path of the X-rays passing through the subject P are described. The distortion of the spectrum is the deviation of the actually detected spectrum 54 from a spectrum expected to be obtained under the ideal condition. For example, the spectrum expected to be obtained under the ideal condition is a spectrum expected to be obtained by an ideal response of the detector 13, being a response calculated by a simple calculation based on Lambert-Beer law and the like, based on the irradiation spectrum 50 and the information on the material in the subject P.

A first factor of causing the distortion of the spectrum includes a distortion of the irradiation spectrum 50 due to the characteristics of the X-ray generator 12. For example, the irradiation spectrum 50 of the X-rays irradiated from an X-ray tube 12a of the X-ray generator 12 is distorted due to the shifting of the focal point of the X-ray emission, and due to the characteristics of a collimator provided on a side of the X-ray tube 12a.

A second factor of causing the distortion of the spectrum includes a distortion of the irradiation spectrum 50 in the path of X-rays, that is a spectrum between the X-ray generator 12 and the subject P. For example, the irradiation spectrum 50 of the X-ray irradiated from the X-ray tube 12a of the X-ray generator 12 is distorted in its irradiation path due to the variability of a mechanical accuracy of a Cu filter provided in the wedge for generating a uniform irradiation spectrum 50.

A third factor of causing the distortion of the spectrum includes a distortion of the transmission spectrum 52 due to beam hardening occurring when the X-rays pass through the subject P. Beam hardening is briefly described below. The absorption of the X-rays passing through the material depends on energy. More specifically, the X-rays with long wavelength and low energy are more absorbed compared with X-rays with high energy. Beam hardening is a phenomenon in which the quality of the X-rays changes due to the point described above, and consequently the linearity of the mass attenuation coefficient is lost. Due to the beam hardening, deviation from the spectrum calculated by the simple calculation appears in the transmission spectrum 52. Hence, the spectrum is distorted in the path of the X-rays passing through the subject P, due to the attenuation of the X-rays passing through the subject. In such a case, the distortion of the spectrum is attributed to the attenuation of the X-ray transmitting through the subject. It is noted that if beam hardening is measured or estimated with precision as the distortion of the energy spectrum, it can be said that the extent of the beam hardening (or the distortion of the spectrum due to the beam hardening only) indicates the composition of the material in the transmission path of the subject.

A fourth factor of causing the distortion of the spectrum includes a distortion of the transmission spectrum 52 due to the scattering occurring when the X-rays pass through the subject P. Typically, the X-rays irradiated from the X-ray tube 12A to the subject P are detected by the detector 13 in the travelling direction of the irradiated X-rays. However, when the scattering occurs, the X-ray irradiated from the X-ray tube 12A onto the subject P have the travelling direction changed within the subject P, and thus is detected by the detector 13 positioned at an angle deviated from the original travelling direction of the irradiated X-rays. As a result, the transmission spectrum is distorted.

A fifth factor of causing the distortion of the spectrum includes a distortion of the transmission spectrum 52 due to a collimator (e.g., post-patient filter) and the like on a side of the detector 13.

A sixth factor of causing the distortion of the spectrum includes response characteristics of the detector 13. More specifically, the detected spectrum 54 actually detected by the detector 13 has a shape obtained by further distorting the transmission spectrum 52. The response characteristics of the detector 13 are, more specifically, each response characteristics of the detection elements 16 of the detector 13. The response characteristics of the detection element 16 are a factor causing the distortion of the transmission spectrum 52 (or the detected spectrum 54) of the X-rays having entered the detection element 16. The response characteristics of the detection element 16 include, for example, escape, fluorescence, crosstalk, and probability of scattering, as well as the variation of the detected energy or the like, for each energy of the X-rays having entered the detection element 16. In this case, the distortion of the spectrum that occurs in the path of the X-rays that have passed through the subject P is attributed to the response characteristics of the X-ray detector 13.

Referring back to FIG. 1, in the X-ray CT apparatus 1 according to the present embodiment, the processing circuitry 35 of the information processing device 30 has specific functions, the details of which are to be described below.

In the description below, an overview of a flow of the entire processing is described, and then each processing step is described in detail. An object of a series of processing executed by the processing circuitry 35 is to accurately calculate the length (X-ray transmission length) travelled by the X-rays having passed through a material of decomposition target in the subject P. However, hampered by the spectrum distortion described above, in some cases, it is difficult to calculate the X-ray transmission from the detected spectrum 54 by a direct solution method.

Thus, in the embodiment, the processing circuitry 35 performs, by the computation function 35C, based on an estimated length indicating a tentative estimate value of the X-ray transmission length of a material of decomposition target included in the subject and information indicating the distortion of the spectrum occurring in the path of the X-rays having passed through the subject, a certain simulation, thereby calculating an estimated spectrum estimated as the spectrum after the X-rays have passed through the subject. Then, the processing circuitry 35 uses the calculation function 35D to compare the estimated spectrum, which is a theoretical value of the detected spectrum 54, with an actually measured value of the detected spectrum 54, which is a spectrum of the X-rays that have passed through the subject and that are detected by the detector 13. More specifically, the processing circuitry 35 uses the calculation function 35D to calculate an error between the estimated spectrum and the detected spectrum 54.

Typically, the processing circuitry 35 calculates the error from the detected spectrum 54, based on estimated spectra calculated for two or more estimated length candidates.

Then, the processing circuitry 35 uses the determination function 35F to determine the X-ray transmission length that is expected to be the closest to the true value, based on the calculated length. For example, the processing circuitry 35 uses the determination function 35F to specify the estimated length in which the error is smallest, out of the errors calculated for the two or more estimated length candidates, as the X-ray transmission length of the material.

Then, the processing circuitry 35 uses the update function 35E to update the value of the estimated length based on the determined X-ray transmission length, the updating value being used as an argument in the next iteration.

The processing circuitry 35 uses the determination function 35F to repeat the series of processing until a predetermined condition is satisfied. As described above, the series of processing includes: updating the estimated length; calculating the estimated spectrum based on the updated estimated length by the computation function 35C; calculating the error by the calculation function 35D; and determining the X-ray transmission length. Then, the processing circuitry 35 uses the determination function 35F to determine the estimated length satisfying the predetermined condition as the X-ray transmission length of the material. The X-ray transmission length of the material thus obtained is the X-ray transmission length of the material to be finally obtained.

It is noted that the processing circuitry 35 may perform the processing described above for a plurality of materials, such as soft tissue and the contrast agent. In such a case, the processing circuitry 35 calculates, for each of the plurality of materials, the estimated spectrum for a plurality of estimated length candidates. The processing circuitry 35 further determines the estimated lengths such that the error is minimized as the X-ray transmission lengths of the materials, based on the estimated spectra calculated.

Next, the functions of the processing circuitry 35 and the procedures of the processing executed by the processing circuitry 35 will be described more in detail.

The reception function 35J receives various operation instructions from the user through the input circuitry 33.

The acquisition function 35B acquires the detected spectrum 54 and an initial value of the estimated length.

As described above, the detected spectrum 54 is a spectrum detected by the detector 13. The acquisition function 35B reads the collection information stored in the storage circuitry 34 by the scan control function 35A. In this manner, the acquisition function 35B acquires the detected spectrum 54 detected by each of the plurality of detection elements 16, at each position of the X-ray generator 12.

The estimated length represents an estimated value of the length (effective length) travelled by the X-rays to pass through the material of decomposition target in the subject P. More specifically, the estimated length is an estimated total value of lengths travelled by the X-rays, irradiated from the X-ray generator 12 to reach the detector 13 after passing through the subject P, through the materials of decomposition target in the optical path of the X-rays.

The estimated length is updated by the update function 35E described later. The initial value of the estimated length acquired by the acquisition function 35B is different from the estimated length updated by the update function 35E.

When the decomposition target includes a plurality of types of materials, the acquisition function 35B acquires the initial value of the estimated length for each of the plurality of types of materials of decomposition target.

For example, the acquisition function 35B acquires the initial value of the estimated length of the material of decomposition target from the input circuitry 33. In the description of the present embodiment, the decomposition target includes a plurality of types of materials. Thus, the acquisition function 35B acquires the initial value of the estimated length for each of the materials, from the input circuitry 33.

The storage circuitry 34 may store in advance, type information indicating the type of each of the plurality of materials and the initial value of the estimated length that are associated with each other. In such a case, for example, the user operates the input circuitry 33 to input the type of the material of decomposition target. The reception function 35J receives the type information indicating the type of the material of decomposition target, input from the input circuitry 33. The acquisition function 35B reads the initial value of the estimated length corresponding to the received type information, from the storage circuitry 34. The acquisition function 35B may acquire the initial value of the estimated length for each of the materials of decomposition target.

The material of decomposition target may be any material involving the attenuation in the spectrum of the X-rays passing therethrough. The material of decomposition target may be an atom, a molecule, or a specific portion or composition of a human body (such as bone and muscle). Examples of the material of decomposition target include water, iodine, calcium, gadolinium, muscle, and fat.

A single type of material or a plurality of types of materials may be the decomposition target. In the description of the present embodiment, the decomposition target includes a plurality of types of materials. In the example described in the present embodiment, the decomposition target includes three types of materials that are water, iodine, and calcium.

For example, the type of the material of decomposition target is input by the user by operating the input circuitry 33. The type information indicating each of the plurality of types of material may be stored in advance in the storage circuitry 34. Thus, the user may operate the input circuitry 33 to issue an instruction for selecting the material corresponding to a desired one of the type information, as the decomposition target. The material of decomposition target may be automatically set based on preset information acquired by the acquisition function 35B from the storage circuitry 34 or the like. The preset information includes information on: medical records and past examination; examination request; and an examined portion.

The update function 35E updates the estimated length to be a more appropriate value as will be described later in detail. Thus, the initial value of the estimated length is preferably a value closer to the actual X-ray transmission length of the material in the subject P. Thus, the acquisition function 35B preferably calculates and thus acquires the initial value of the estimated length of the material of decomposition target.

The calculation of the initial value by the acquisition function 35B as described above facilitates an attempt to achieve smaller repeated times of the series of processing described below, and to achieve more accurate and stable determination of the X-ray transmission length of the material by the determination function 35F described below.

For example, the acquisition function 35B may calculate and thus acquire the initial value of the estimated length of the material of decomposition target by using a already-known method. For example, the acquisition function 35B may calculate the thickness of the material with a method disclosed in Japanese Patent Application Laid-open No.

5-161633, based on the detected spectrum 54 and the average absorption coefficient of each of the material of decomposition target. Then, the acquisition function 35B may use the thickness of the material thus calculated as the initial value of the estimated length of the material of decomposition target.

For example, the acquisition function 35B may generate an X-ray CT image based on the irradiation spectrum 50 and the detected spectrum 54, and simply calculate the initial value from the X-ray CT image thus generated. For example, the acquisition function 35B generates the X-ray CT image based on the total number of photon counts or the effective energy of each of the irradiation spectrum 50 and the detected spectrum 54. In this process, the X-ray CT image is preferably generated by using all the energy bands of the irradiation spectrum 50 and the detected spectrum 54. Thus, the influence of the response characteristics of the detector 13 can be offset, and information with high SN ratio can be used. The acquisition function 35B obtains the initial value of water, as one of the decomposition materials, by dividing the sum of CT values (linear attenuation coefficient) in the optical path of the X-rays by the average linear attenuation coefficient of water. The acquisition function 35B sets the initial value of the other materials of decomposition target to be zero. Thus, a simply estimated initial value can be obtained for a hypothetical case where the subject is made of water only.

The acquisition function 35B may execute threshold processing on the CT values in the X-ray CT image, to extract only a high luminance area corresponding to a bone, a contrast medium, or the like. The acquisition function 35B may use an initial value simply estimated by allocating the sum of the CT values, in the optical path of the X-rays in the extracted area, to iodine and calcium. The X-ray CT image can be relatively accurately classified into four areas of an air area, a fat area, a muscle/blood area, and a bone/contrast medium area, with fixed thresholds. Various methods for actively determining the threshold by using CT value histogram information have been proposed.

In a case in which the acquisition function 35B calculates the initial value of the estimated length with the method disclosed in Japanese Patent Application Laid-open No. 5-161633, it is preferable that the plurality of positions of the X-ray generator 12 and the plurality of positions of the detection elements 16 be classified into a plurality of groups and that the calculation be performed for each of the plurality of groups. By calculating for each group, it becomes possible to improve stability by improving SN ratio and to shorten the computation time by reducing the number of computations to be performed.

The computation function 35C computes an estimated spectrum. The estimated spectrum is a spectrum of the X-rays that have passed through the subject P and is a spectrum detected by the detector 13.

The computation function 35C computes the estimated spectrum based on the irradiation spectrum 50, the estimated length, and response information.

The response information indicates distortion of the spectrum arising from the response characteristics of the detector 13 and the like. The response characteristics have already been described above, and thus the description thereof is omitted herein. The response information may be stored in advance in the storage circuitry 34. For example, the response information is stored in advance in the storage circuitry 34 while being associated with the identification information of the detection element 16.

The irradiation spectrum 50 may be stored in advance in the storage circuitry 34. For example, the irradiation spectrum 50 is stored in advance in the storage circuitry 34 while being associated with the position of the X-ray generator 12 and the position of the detection element 16. The irradiation spectrum 50 does not change in accordance with the position of the X-ray generator 12. Thus, the storage circuitry 34 may store therein in advance, only the irradiation spectrum 50 of a type corresponding to the position of the detection element 16.

The computation function 35C computes the estimated spectrum by using the estimated length, the response information, and the irradiation spectrum 50 for each of the plurality of detection elements 16 for each position of the X-ray generator 12.

FIG. 3 is a diagram schematically illustrating the processing executed by the processing circuitry 35.

For example, it is assumed that the computation function 35C performs the calculation by using the irradiation spectrum 50 corresponding to a shape in graph A in FIG. 3. Further, it is assumed that the transmission spectrum 52, being a spectrum of the X-rays that are represented by the irradiation spectrum 50 and that have passed through the subject P, is the spectrum illustrated in graph B in FIG. 3. It is assumed that the detected spectrum 54, being a spectrum actually detected by the detection element 16, has a spectrum illustrated in graph C in FIG. 3.

In this case, the computation function 35C computes the estimated spectrum 56 based on the irradiation spectrum 50, the estimated length, and the response information (see graph D in FIG. 3).

In more detail, the computation function 35C computes the estimated spectrum 56, by attenuating the irradiation spectrum 50 in accordance with the linear attenuation coefficient and the estimated length of the material of decomposition target, and by distorting the resultant spectrum in accordance with the distortion indicated by the response information.

A linear attenuation coefficient of a material is a linear attenuation coefficient of a material of decomposition target with respect to the energy of the X-ray. The linear attenuation coefficient of a material for each energy of the X-rays may be stored in advance in the storage circuitry 34.

For example, the storage circuitry 34 stores therein in advance, the type information indicating the type of the material, the X-ray energy, and the linear attenuation coefficient associated with each other. The computation function 35C may read the linear attenuation coefficient that corresponds to the type information of the material of decomposition target from the storage circuitry 34, thereby computing the estimated spectrum 56.

First of all, a case is described in which the reason the distortion of the spectrum arises is the sixth factor described above, that is, a case in which computation of the estimated spectrum 56 considering the distortion of the spectrum arising from the response characteristics of the detector 13 is performed. In such a case, the processing circuitry 35 uses the computation function 35C to calculate the estimated spectrum 56, based on the response characteristics of the detector 13 as information indicating the distortion of the spectrum and the estimated length.

More specifically, the computation function 35C computes the estimated spectrum 56 by performing the arithmetic operation represented by Formula (3) below.

$$s_2(c, v, e) = F_{c,e}\left(s_0(c, e)\exp\left(-\sum_{m=1}^{N_M} \mu_m(e)l_m(c, v)\right)\right) \quad (3)$$

In Formula (3), c is the same as those in Formula (1) and Formula (2), e is the same as that in Formula (1), and v is the same as that in Formula (2).

In Formula (3), m represents a serial number provided to each type of material of decomposition target, and $N_M$ represents the number of materials of decomposition target (number of types). As described above, in the example described in the present embodiment, the decomposition target includes the three types of materials that are water, iodine, and calcium. Thus, in this example, a case in which $N_M$=3 is explained, where m=1 represents water, m=2 represents iodine, and m=3 represents calcium.

In Formula (3), $\mu_m$ represents the linear attenuation coefficient of a material of decomposition target m, $l_m$ represents the estimated length of the material of decomposition target m, and $F_{c,e}$ represents the response information on the detector 13. More specifically, $F_{c,e}$ represents the response information on the detection element 16 at the position c with respect to the energy e of the X-ray.

Furthermore, $S_2(c,v,e)$ represents the estimated spectrum 56. More specifically, $S_2(c,v,e)$ represents the group of estimated values of the numbers of photon counts, with respect to the energy e, of the X-rays detected by the detection element 16 at the position c when the X-ray generator 12 is at the position v.

Thus, a portion other than $F_{c,e}$ in the right side of Formula (3) indicates the spectrum obtained by attenuating the irradiation spectrum 50 that is represented by $S_0(c,e)$, by the estimated length $l_m$ of each material of decomposition target and the linear attenuation coefficient. The estimated spectrum 56, represented by $S_2(c,v,e)$, is calculated by distorting the spectrum by the distortion represented by the response information $F_{c,e}$.

As described above, in Formula (3), e is the same as that in Formula (1). Thus, the energy width of the energy e used for calculating the estimated spectrum 56 is the same as the second energy width E2 (see FIG. 2B) of the irradiation spectrum 50.

Thus, as described above, in the present embodiment, e=1 in Formula (3) represents the energy band in a range between 0 keV inclusive and 1 keV exclusive, and e=2 represents the energy band in a range between 1 keV inclusive and 2 keV inclusive. Similarly, e=100 represents the energy band in a range between 99 keV inclusive and 100 keV inclusive.

The computation function 35C may read the linear attenuation coefficient from the storage circuitry 34, and use the linear attenuation coefficient for the calculation. Thus, the storage circuitry 34 may store therein in advance, the linear attenuation coefficient corresponding to each of the energy bands corresponding to the numbers of photon counts in the estimated spectrum 56. For example, the storage circuitry 34 may store therein in advance, the linear attenuation coefficient corresponding to the center value of the upper limit value and the lower limit value of each energy band, for each material of decomposition target. For example, the center value of the upper limit value and the lower limit value is 99.5 keV when the energy band is in the range between 99 keV inclusive and 100 keV inclusive.

As described above, in the description of the present embodiment, the first energy width E1 and the second energy width E2 are the same. Thus, in the description of present embodiment, the computation function 35C calculates the estimated spectrum 56 by Formula (3) described above. When the first energy width E1 is larger than the second energy width E2, the right side of Formula (3) may be normalized (average operation is performed) so as to correspond to the first energy width E1. It is noted that known methods may be employed for the normalization.

It is noted that in some cases the response information varies depending on the number of photons entering the detector 13 in each unit time. For example, when the photons successively enter the detector 13, the response of the detector 13 becomes insufficient. Consequently, in some cases, the photons may be counted as the photons of lower energy (or higher energy) than their actual energy. Thus, the computation function 35C may use the response information corresponding to the number of photon counts indicated by the detected spectrum 54, to compute the estimated spectrum 56.

In such a case, the storage circuitry 34 may store therein in advance, response information corresponding to each of the position of the detection element 16 and the number of photon counts.

Next, a case is briefly explained in which the estimated spectrum 56 taking the distortion of the spectrum into consideration is computed, when the reason the distortion of the spectrum arises is the reason of either one of the first to fifth factors described above.

When the spectrum is distorted by the first factor (focal point transition in X-ray irradiation, the collimator characteristics on the side of the X-ray tube and the like) or the second factor (the wedge and the like), in which case the X-ray tube side is responsible, the processing circuitry 35 uses the computation function 35C to calculate the estimated spectrum 56 by evaluating the right side of Formula (3), by using a formula obtained by replacing $s_0(c,e)$ with $F_1(s_0(c, e))$ in Formula (3), where $F_1$ represents a function indicating the distortion of the irradiation spectrum 50 caused by the first or the second factor. A specific expression of such function, is retained in the storage circuitry 34 in the form of a predetermined table. It is noted that when no correction due to the sixth factor described above is performed, $F_{c,e}$=1 holds true.

When the spectrum is distorted by the fifth factor (the collimator on the side of the detectors), in which case the detector side is responsible, the processing circuitry 35 uses the computation function 35C to compute the estimated spectrum 56, by evaluating the right side of Formula (3), taking this effects into the expression $F_{c,e}$ in Formula (3). A specific expression of such function is retained in the storage circuitry 34, for example, in the form of a predetermined table.

When the spectrum is distorted by the third factor (beam hardening), the processing circuitry 35 can generate a table indicating the change in the spectrum due to beam hardening, by using, for example, a Monte Carlo simulation. By virtue of such table, the energy dependence of X-ray attenuation originating from the material composition of the subject can be known. Based on this, an estimate of the material composition becomes possible. The processing circuitry 35 stores the table thus generated in the storage circuitry 34. When the processing of capturing an image of the subject P is executed, the processing circuitry uses the computation function 35C to calculate the estimated spectrum 56 based on the table stored in the storage circuitry 34 and the estimated length. In such a case, the table described above (information indicating attenuation of the X-rays passing through the subject) serves as an example of information indicating the distortion of the spectrum. In such case, embodiments do not require a Monte Carlo simulation and such a table may be generated by a simpler method.

Further, when the spectrum is distorted by the fourth factor (scattering) described above, the X-ray tube 12A irradiates the X-ray corresponding to the already-known irradiation spectrum 50 onto the already-known material such as a phantom. The detector 13 detects the detected spectrum 54. As the effect of scattering is included in the detected spectrum 54, the processing circuitry 35 can generate a scattering information table indicating the scattering effect, based on information on a material of the phantom, the irradiation spectrum 50, and the detected spectrum 54. The processing circuitry 35 stores the scattered information table thus generated in the storage circuitry 34. When processing regarding the acquisition of an image of the subject P is executed, the processing circuitry 35 uses the computation function 35C to calculate the estimated spectrum 56 based on the scattering information table stored in the storage circuitry 34 and the estimated length. In such a case, the scattering information table (the scattering characteristics of the X-ray) serves as an example of information indicating the distortion of the spectrum.

Next, the calculation function 35D is described. The calculation function 35D calculates the error between the estimated spectrum 56 and the detected spectrum 54.

More specifically, the calculation function 35D calculates the error between the estimated spectrum 56 and the detected spectrum 54 for each detection element 16 and for each position of the X-ray tube 12A. The calculation function 35D calculates the error for each combination of the estimated spectrum 56 and the detected spectrum 54 corresponding to the same position of the X-ray generator 12 and the detection element 16 of the same position.

It is noted that a series of processing including updating of the estimated length by the update function 35E described below, the calculation of the estimated spectrum 56 by the computation function 35C, and the calculation of the error by the calculation function 35D, is repeatedly executed by the determination function 35F to be described below (described later in detail).

For this reason, the calculation function 35D uses the estimated spectrum 56 computed immediately before by the computation function 35C as an object for calculating the error. In other words, every time the computation function 35C newly calculates the estimated spectrum 56, the calculation function 35D calculates the error from the detected spectrum 54 using the newly calculated estimated spectrum 56.

For example, the calculation function 35D calculates the error based on the difference between the detected spectrum 54 and the estimated spectrum 56 in the number of photon counts in each energy. More specifically, the calculation function 35D calculates, as the error, an integrated value (for example, mean square value) of difference between the detected spectrum 54 and the estimated spectrum 56 in the number of photon counts with respect to the energy.

To describe in more detail, the calculation function 35D calculates, as the error, an integrated value of the errors between the detected spectrum 54 and the estimated spectrum 56 in the number of photon counts corresponding to each energy band with the second energy width E2.

More specifically, for example, the calculation function 35D calculates the error by Formula (4) described below.

$$d = \sum_{e=1}^{N_E} (s_1(c, v, e) - s_2(c, v, e))^2 \qquad (4)$$

In Formula (4), d represents the error, $S_1(c,v,e)$ is the same as that in Formula (2) described above, $S_2(c,v,e)$ is the same as that in Formula (3) described above, and c, e, and v are the same as those in Formula (3).

In Formula (4), $N_E$ represents the upper limit value of the energy e. For example, in an example described in the present embodiment, $N_E=120$ holds true.

The calculation function 35D may calculate the error by Formula (5) described below.

$$d = \sum_{e=E_{min}}^{E_{max}} (s_1(c, v, e) - s_2(c, v, e))^2 \qquad (5)$$

In Formula (5), d, $S_1(c,v,e)$, $S_2(c,v,e)$, c, e, and v are the same as those in Formula (4), $E_{min}$ represents a value larger than the energy corresponding to the smallest possible number of photons detectable by the detector 13, and $E_{max}$ represents a value smaller than the energy corresponding to the largest possible number of photons detectable by the detector 13.

In other words, as indicated by Formula (5), the calculation function 35D may limit the range of energy used for calculating the error to an appropriate energy range between $E_{min}$ inclusive and $E_{max}$ inclusive.

The calculation function 35D may calculate the error with any one of Formula (6), Formula (7), and Formula (8) described below.

$$d = \sum_{e=E_{min}}^{E_{max}} a(e)(s_1(c, v, e) - s_2(c, v, e))^2 \qquad (6)$$

$$d = \sum_{e=E_{min}}^{E_{max}} a(e)(g*s_1(c, v, e) - g*s_2(c, v, e))^2 \qquad (7)$$

$$d = \sum_{b=1}^{N_B} a(b) \left( \sum_{e=E_0(b)}^{E_1(b)} s_1(c, v, e) - \sum_{e=E_0(b)}^{E_1(b)} s_2(c, v, e) \right)^2 \qquad (8)$$

In Formula (6) to Formula (8), d, $S_1(c,v,e)$, $S_2(c,v,e)$, c, e, v, $E_{min}$, and $E_{max}$ are the same as those in Formula (5) described above. A function g is a predetermined function used as a filter function, and an operator "*" indicates a convolution operation.

In Formula (6), a(e) represents a weighting coefficient corresponding to the energy e. An appropriate value may be set in advance as the weighting coefficient for each energy.

In other words, the calculation function 35D calculates the error between the estimated spectrum and the detected spectrum based on: the difference between the detected spectrum 54 and the estimated spectrum 56 in the number of photon counts for each energy; and the weighting coefficient corresponding to the energy based on the characteristics of the material of decomposition target. In one example, as in Formula (6), the calculation function 35D calculates the error between the estimated spectrum and the detected spectrum based on a linear sum of a square of the difference between the detected spectrum 54 and the estimated spectrum 56 in the number of photon counts for each energy and the weighting coefficient corresponding to the energy based on the characteristics of the material of decomposition target.

For example, an energy band expected to be important for calculating the error is set in advance. Then, the calculation function 35D may set a higher weighting coefficient to energy in the energy band, compared with energy not in the energy band.

In one example, the calculation function 35D calculates the error based on such a weighting coefficient that the weighting coefficient for an energy with an energy difference from a predetermined energy not exceeding a first threshold is smaller than a weighing coefficient of other energies. Here, for example, the predetermined energy is the energy corresponding to the K-edge. The reason why such a weighting coefficient is used is as follows: Energy areas close to the K-edge tend to accumulate errors in the detected spectrum 54 and thus, the weighting coefficient within this energy region is preferably set to be small. Thus, the calculation function 35D sets a small weighting coefficient for the energy region in the vicinity of the K-edge.

In another example, the calculation function 35D calculates the error based on such a weighting coefficient that the weighting coefficient for an energy with an energy difference from a predetermined energy being equal to or larger than a first threshold and with an energy difference from the predetermined energy being equal to or smaller than a second threshold is larger than weighting coefficients of other energies. Here, for example, the predetermined energy is the energy corresponding to the K-edge. The reason why such a weighting coefficient is used is as follows: When the energy region close to the K-edge described above is excluded, the X-ray transmission length can be estimated more accurately for energy closer to the K-edge. Thus, the calculation function 35D sets the weighting coefficient to be large for an energy region corresponding to the energy with an energy difference from the K-edge being larger than the first threshold and with an energy difference from the K-edge being equal to or smaller than the second threshold. In other words, as the spectrum information in the vicinity of the K-edge is useful for material decomposition, it is desirable that large weighting coefficients be employed for this region. However, as for the region closest to the K-edge (the energy difference from the K-edge is equal to or smaller than the first threshold), small weighting coefficients are employed, as there is a possibility that the error becomes large.

Further, the first threshold may be "zero". In such a case, the calculation function 35D calculates the error based on such a weighting coefficient that the weighting coefficient for an energy with an energy difference from the predetermined energy being equal to or smaller than the second threshold is larger than a weighting coefficient of other energies.

Further, a value corresponding to energy based on the characteristics of the material of decomposition target may be set as the weighting coefficient. The characteristics of the material of decomposition target include attenuation characteristics of the material for the X-ray and/or K-edge energy.

For example, the calculation function 35D sets in advance, an area of an energy band with an attenuation rate being equal to or larger than a threshold or being smaller than the threshold, that is indicated by the attenuation characteristics for the X-rays of at least one of a plurality of types of materials of decomposition target. The threshold may be set to be an appropriate value, and may be updated by a user operation on the input circuitry 33. The calculation function 35D may set in advance a higher weighting coefficient for the energy in the resultant energy band, compared with energies not in the energy band.

For example, a higher weighting coefficient may be set for an energy band including the K-edge (for example, around 33 keV in the case of iodine) of the material of decomposition target, compared with the energy not in the energy band.

All things considered, the calculation function 35D may calculate the error as an integrated value of errors between the detected spectrum 54 and the estimated spectrum 56 in the number of photon counts for each energy, incorporating the weighting coefficients dependent on the energy derived based on the characteristics of the material.

As in Formula (7), the calculation function 35D may calculate the error by performing a convolution operation further using the function g, so that the influence of noise in the detected spectrum 54 and the like can be taken into account.

Examples of the function g include: a linear filter such as a mean filter or a Gaussian filter; and a nonlinear filter such as a ε filter. Filter parameters, such as a filter size (range) and ε, of each filter are preferably switched between energies, so that blurring can be restrained in the energy around 33 keV as the K-edge of iodine.

Thus, the calculation function 35D may use the function g in Formula (7) to adjust the filter range for the detected spectrum 54 and the estimated spectrum 56 with which the error is calculated, so that the spectrum is restrained from blurring around the 33 keV.

In Formula (8), b represents a serial number of each of a plurality of groups each including a predetermined number of (two or more) consecutive energies e. For example, the serial number of each group may be allocated in such a manner that a group with a larger energy e is allocated with a larger numerical value representing the serial number. In Formula (8), $N_B$ represents the number of groups.

In Formula (8), $E_0$ and $E_1$ respectively represents a lower limit value and an upper limit value of the energy e in the group b. For example, $E_0(1)=1$, $E_1(1)=20$, $E_0(2)=21$, $E_1(2)=40$, . . . hold true and $N_B=6$ also holds true.

Thus, as indicated by Formula (8), the calculation function 35D may calculate the error as the difference between the estimated spectrum 56 and the detected spectrum 54 in the sum of the numbers of photon counts in an appropriate energy range (range between $E_0(b)$ and $E_1(b)$, inclusive).

The update function 35E updates the estimated length. More specifically, the update function 35E updates the estimated length corresponding to the estimated spectrum 56 used in the previous calculation for the error by the calculation function 35D. The estimated length corresponding to the estimated spectrum 56 used in the previous calculation for the error is an estimated length used by the computation function 35C for calculating the estimated spectrum 56. The estimated length corresponding to the estimated spectrum 56 used in the previous calculation for the error may be hereinafter abbreviated as a previously used estimated length in some cases.

A method of updating the previously used estimated length by the update function 35E is described later.

It is noted that the update by the updating function 35E means to further store to the storage circuitry 34 the estimated distance after the estimated value has been changed, while keeping the estimated distance already stored in the storage circuitry intact. Thus, an updated estimated length is newly stored in the storage circuitry 34, each time the update function 35E updates the estimated length.

The determination function 35F determines the X-ray transmission length of the material, based on the error calculated by the calculation function 35D.

For example, the determination function 35F determines such an estimated length that the error calculated by the calculation function 35D does not exceed the threshold, as the X-ray transmission length of the material.

In the present embodiment, the determination function 35F controls the update function 35E, the computation function 35C, and the calculation function 35D in such a manner that a series of processing, including updating the estimated length, calculating the estimated spectrum 56 based on the updated estimated length, and calculating the error, is repeated.

As illustrated in FIG. 3, with the control thus performed by the determination function 35F, the estimated length is updated each time the series of processing is executed (see a panel E in FIG. 3). In a panel E in FIG. 3, L1 represents an example of the estimated length of water as the material of decomposition target, L2 represents an example of the estimated length of iodine, and L3 represents the estimated length of calcium.

All things considered, the determination function 35F repeatedly executes the series of processing including: updating the estimated length (see the panel E in FIG. 3); calculating the estimated spectrum 56 based on the irradiation spectrum 50 (see the graph A in FIG. 3) and the updated estimated length (see the graph D in FIG. 3); and calculating the error between the estimated spectrum 56 and the detected spectrum 54 (see the graph C in FIG. 3).

Referring back to FIG. 1, the determination function 35F specifies the estimated length used in the series of processing resulting in the calculation of an error not exceeding the threshold, as the X-ray transmission length of the material.

Thus, the determination function 35F controls the update function 35E, the computation function 35C, and the calculation function 35D such that the series of processing, including updating the estimated length, calculating the estimated spectrum 56 based on the updated estimated length, and calculating the error, is repeated until the error not exceeding the threshold is calculated.

The threshold used by the determination function 35F may be set to be a value available for determining whether the error and the estimated length have been optimized. For example, the threshold used by the determination function 35F may be the smallest value of the errors calculated by repeating the series of processing. In such a case, the determination function 35F specifies the smallest value of the errors calculated by repeating the series of processing as the error not exceeding the threshold. Then, the determination function 35F may specify the estimated length used in the series of processing with the calculated error not exceeding the threshold as the X-ray transmission length of the material. In other words, the determination function 35F may specify the estimated length in which the error is smallest as the X-ray transmission length of the material.

The update function 35E preferably updates the previously used estimated length in such a manner that an error smaller than the previously calculated error is calculated each time the series of processing is executed. The method of updating the estimated length by the update function 35E may be a known optimization method such as greedy method, steepest descent method, or conjugate gradient method.

Typically, in performing optimization, the processing circuitry 35 uses the calculation function 35D to calculate an error for two or more estimated length candidates.

In such a case, when the processing circuitry 35 uses greedy method by the determination function 35F, for example, an estimated length candidate with the smallest error among errors calculated for the two or more estimated length candidates becomes the estimated length in the subsequent iteration step.

When computation of differential coefficients are required in updating the iteration step, such as in the case of steepest descent method and the like, the processing circuitry 35 uses the determination function 35F to calculate the differential coefficient by using difference calculus for the errors calculated for the two or more estimated length candidates, and calculate the estimated length in the subsequent iteration step by using the differential coefficient thus calculated.

With the control performed by the determination function 35F as described above, the estimated length is updated each time the series of processing is executed. The calculation function 35D may change the weighting coefficient (see a(e) in Formula (6) and Formula (7) described above) used for calculating the error, $E_{min}$, $E_{max}$, $E0(b)$, and $E1(b)$ indicating the energy range, and the filter function g, in accordance with the updated estimated length.

For example, let us assume that the estimated length of iodine is the largest among the updated estimated lengths of the materials of decomposition target. In such a case, it is preferable that the difference between the detected spectrum 54 and the estimated spectrum 56 calculated in the subsequent series of processing in the number of photon counts around 33 keV as the K-edge of iodine, be smaller than that calculated in the current series of processing.

In such a case, the calculation function 35D preferably sets the weighting coefficient a(e), in each of Formula (6) and Formula (7) described above, to be larger for the energy band around 33 keV, than for energy not in the energy band.

The calculation function 35D may limit the appropriate energy range indicated by $E_{min}$ and $E_{max}$ in Formula (5) described above, to be around 33 keV.

As described above, the calculation function 35D updates the weighting coefficient in accordance with the updated estimated length, thereby amplifying the effect of the difference of the number of photon counts in the vicinity of 33 keV on the errors.

Further, the calculation function 35D is preferably designed in such a manner that 33 keV is included in an energy band indicated by $E_0$ and $E_1$ in Formula (8), and defined by the lower limit value and the upper limit value of the energy e in the group b.

On the other hand, let us assume that the estimated length of iodide is the smallest out of the updated estimated lengths of the material of decomposition target. In such a case, it is preferable that the calculation function 35D sets the weighting coefficient a(e), in each of Formula (6) and Formula (7) described above, be smaller for the energy band around 33 keV, than for energy not in the energy band.

In such a case, the calculation function 35D changes the weighting coefficient in accordance with the updated estimated length, thereby suppressing the effects of the difference of the number of phonon counts in the vicinity of 33 keV on the errors. Thus, in this case, the effects of the difference of the number of phonon counts in the vicinity of 33 keV, that has small number of photons to be transmitted and is susceptible to the noise, on the errors to be subsequently calculated, can be suppressed. In other words, in this case, the degradation of the accuracy of error calculation can be suppressed.

Next, the reconstruction function 35H is described. The reconstruction function 35H reconstructs a CT image with a already-known reconstruction method using the detected spectrum 54 that is detected by each detection element 16, for each position of the X-ray generator 12 and acquired by the acquisition function 35B. An example of the reconstruction method includes back projection processing. An example of the back projection processing includes filtered back projection (FPB).

The generation function 35G generates a display image that is in accordance with the X-ray transmission length determined by the determination function 35F.

The display image further includes at least one of: the X-ray transmission length of each material of decomposition target determined by the determination function 35F; the density of the material calculated from the X-ray transmission length; the type of the material of decomposition target; and an atomic number of the material of decomposition target.

For example, the generation function 35G calculates a density distribution of the materials of decomposition target in the subject P. The calculation is performed by using the X-ray transmission length of each of the materials of decomposition target (for example, water, iodine, and calcium) that is determined for each detection element 16 of the detector 13 and corresponds to each position of the X-ray generator 12. The density distribution may be calculated with a already-known method.

For example, the generation function 35G generates the display image as a color image obtained by allocating the density distribution of water to a G channel, allocating the density distribution of iodine to an R channel, and allocating the density distribution of calcium to a B channel.

The generation function 35G may also generate the display image as a color image in which the density of each of the material of decomposition target in the subject P is indicated by a color and a thickness of the color representing the level of the density.

The generation function 35G may generate a display image as a monochrome X-ray CT image or an X-ray CT image including high energy bands only, generated from the image indicating the density of the materials in the subject P.

The generation function 35G may generate the display image as a composite image made of the color image and the CT image generated by the reconstruction function 35H. In such a case, the generation function 35G may generate the composite image (display image) through a blending of the CT image and the color image.

The display control function 35I performs control such that various images are displayed on the display 32. In the present embodiment, the display control function 35I performs the control such that the display image generated by the generation function 35G and the CT image generated by the reconstruction function 35H are displayed on the display 32.

Figure 4:
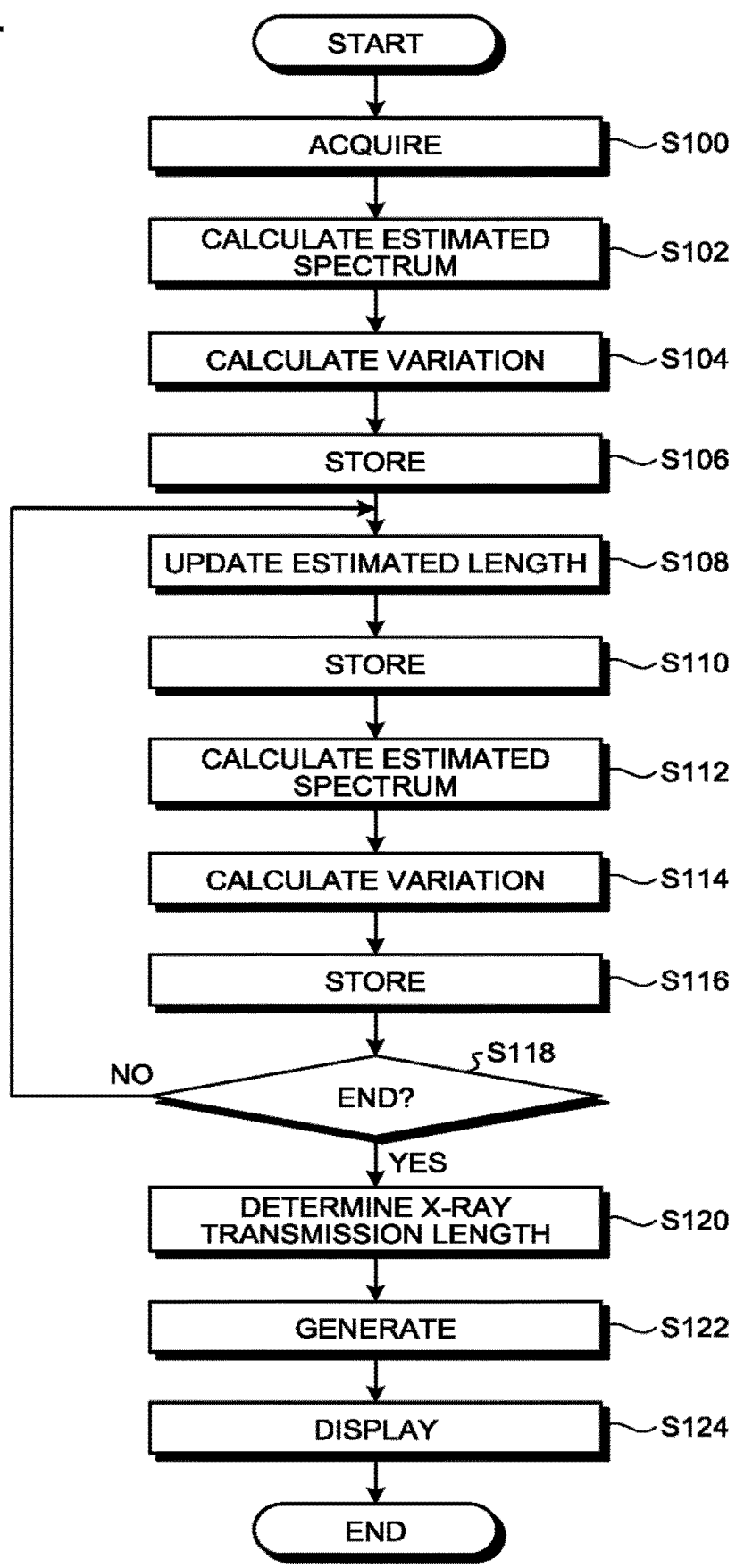
FIG. 4 is a flowchart illustrating an example of a procedure of decomposition processing.

Next, a procedure of the decomposition processing executed by the processing circuitry 35 is described. FIG. 4 is a flowchart illustrating an example of the procedure of the decomposition processing executed by the processing circuitry 35.

First of all, the acquisition function 35B acquires the detected spectrum 54 and the initial value of the estimated length (step S100).

Then, the computation function 35C calculates the estimated spectrum 56 based on the irradiation spectrum 50, the initial value of the estimated length acquired at step S100, and the response information (step S102).

Then, the calculation function 35D calculates the error between the estimated spectrum 56 calculated at step S102 and the detected spectrum 54 acquired at step S100 (step S104). The error calculated at step S104 is stored in the storage circuitry 34 by the calculation function 35D, while being associated with the estimated length acquired at step S100 (step S106).

Then, the update function 35E updates the estimated length (step S108). The update function 35E updates the estimated length most recently stored in the storage circuitry 34. The update function 35E newly stores the updated estimated length in the storage circuitry 34 (step S110).

Then, the computation function 35C calculates the estimated spectrum 56 based on the irradiation spectrum 50, the updated estimated length obtained at step S108, and the response information (step S112).

Then, the calculation function 35D calculates the error between the estimated spectrum 56 calculated at step S112 and the detected spectrum 54 acquired at step S100 (step S114). The error calculated at step S114 is stored in the storage circuitry 34 by the calculation function 35D, while being associated with the updated estimated length obtained at step S108 (step S116).

For this reason, the error between the detected spectrum 54 and the estimated spectrum 56 and the estimated length of each material of decomposition target are sequentially stored while being associated with each other in the storage circuitry 34, as the series of processing including step S108 to step S116 is repeated.

Subsequently, the determination function 35F determines whether the processing is to be terminated (step S118). For example, the determination function 35F determines whether the series of processing including step S108 to step S116 is repeated for a predetermined number of times, thereby performing the determination at step S118.

The determination function 35F may determine whether a signal instructing the termination of the processing has been received by the reception function 35J from the input circuitry 33, thereby performing the determination at step S118. The determination function 35F may determine whether the error calculated at step S114 is equal to or smaller than the above-described threshold used by the determination function 35F, thereby performing the determination at step S118.

The determination function 35F may determine whether the difference between the error calculated at step S114 and the error calculated previously is within a predetermined fluctuation range, thereby performing the determination at step S118.

When the result of the determination at step S118 is No (step S118: No), the processing returns to step S108. Thus, the determination function 35F performs control such that processing from step S108 to step S118 (Steps corresponding to "No") is repeated. More specifically, the determination function 35F controls the update function 35E, the computation function 35C, and the calculation function 35D such that the series of processing, including updating the estimated length, calculating the estimated spectrum 56 based on the updated estimated length, and calculating the error by using the estimated spectrum 56 is repeated.

When the result of the determination at step S118 is Yes (step S118: Yes), the processing proceeds to step S120.

At step S120, the determination function 35F determines the X-ray transmission length of the material (step S120).

For example, the determination function 35F determines, from the storage circuitry 34, the smallest error out of errors that are calculated by the series of processing from step S108 to step S116 described above and that are stored in the storage circuitry 34. Then, the determination function 35F reads from the storage circuitry 34 the estimated length corresponding to the smallest error thus determined. Thus, the determination function 35F determines the estimated length corresponding to the smallest error thus determined as the X-ray transmission length of the material. In other words, the determination function 35F may determine the X-ray transmission length of each of the materials of decomposition target.

The determination function 35F may determine the error calculated by the series of processing with result of the determination at step S118 indicating that the series of processing has been repeated for the predetermined number of times, among the errors that are calculated by repeating the series of processing from step S108 to step S116 and that are stored in the storage circuitry 34. The determination function 35F reads, from the storage circuitry 34, the estimated length corresponding to the smallest error thus determined. By this processing, the determination function 35F may determine the estimated length when the series of processing described above has been repeated for a predetermined number of times, as the X-ray transmission length of the material.

Further, let us assume that at step S118, the determination function 35F determines whether the difference from the previously calculated error is within the predetermined fluctuation range, thereby performing the determination at step S118. In this case, the determination function 35F may determine the estimated length corresponding to the error calculated by the processing with Yes as the result of the determination at step S118, as the X-ray transmission length of the material. As described above, the determination function 35F may determine the estimated length with the difference in the calculated error within the predetermined fluctuation range, as the X-ray transmission length of the material.

The X-ray transmission length thus determined is stored in the storage circuitry 34 by the determination function 35F while being associated with the type information indicating the type of the corresponding material.

Next, the generation function 35G generates the display image that is in accordance with the X-ray transmission length of each material stored in the storage circuitry 34 at step S120 (step S122). Then, the display control function 35I displays the display image, generated at step S122, on the display 32 (step S124). Thus, this routine is completed.

The processing at step S122 and step S124 may be executed when the user operates the input circuitry 33 to issue an instruction to display the display image.

As described above, the X-ray CT apparatus 1 according to the present embodiment includes the computation function 35C, the calculation function 35D, and the determination function 35F. The computation function 35C calculates the estimated spectrum 56 of the X-rays that have passed through the subject P and that are detected by the detector 13. The calculation is based on the irradiation spectrum 50, the estimated length, and the response information. The irradiation spectrum 50 corresponds to the X-rays irradiated to the subject P from the X-ray generator 12. The estimated length represents the estimated value of the X-ray transmission length of a material of decomposition target. The response information indicates the distortion of the spectrum arising from the response characteristics of the detector 13 detecting the X-rays. The calculation function 35D calculates the error between the estimated spectrum 56 and the detected spectrum 54 corresponding to the X-rays that have passed through the subject P and that have been detected by the detector 13. The determination function 35F determines the X-ray transmission length of the material based on the error.

As described above, the X-ray CT apparatus 1 according to the present embodiment calculates the error between the estimated spectrum 56 calculated from the irradiation spectrum 50 based on the estimated length and the response information and the detected spectrum 54 that is an actually detected spectrum. The X-ray CT apparatus 1 determines the X-ray transmission length of the material based on the error.

Thus, the X-ray CT apparatus 1 according to the present embodiment can reduce the influence of the estimation error compared with a case where the estimated spectrum 56 is estimated from the detected spectrum 54 or the other like cases.

Thus, the X-ray CT apparatus 1 according to the present embodiment can perform highly accurate material decomposition.

The determination function 35F may specify the X-ray transmission length of the material as the estimated length with the error not exceeding the threshold. The determination function 35F may determine the X-ray transmission length of the material as the estimated length with the smallest error.

The determination function 35F may determine the X-ray transmission length of the material as the estimated length with the difference in the calculated error within the predetermined fluctuation range. The determination function 35F may determine the X-ray transmission length of the material as the estimated length calculated in the final one of the series of processing repeated for a predetermined number of times. The series of processing includes updating the estimated length, calculating the estimated spectrum 56 based on the updated estimated length, and calculating the error.

The initial value of the estimated length, used by the computation function 35C to calculate the estimated spectrum 56 for the first time, takes into account the influence of the beam hardening effect, the response characteristics of the detection element 16, and the like. Still, the X-ray CT apparatus 1 according to the present embodiment specifies the estimated length with the error not exceeding the threshold, the estimated length with the smallest error, the estimated length with the difference in the error not exceeding the predetermined fluctuation range, or the estimated length calculated in the final one of the series of processing repeated for the predetermined number of times. Thus, the X-ray CT apparatus 1 can achieve highly accurate material decomposition.

In the present embodiment, the first energy width E1 represents the energy width of the energy band corresponding to each number of photon counts indicated by the detected spectrum 54 used by the information processing device 30 (see FIG. 2D). The second energy width E2 represents the energy width of the energy band corresponding to each number of photon counts indicated by the irradiation spectrum 50 (see FIG. 2B). In the present embodiment, the second energy width E2 is equal to or smaller than the first energy width E1.

The first energy width E1 and the second energy width E2 are each smaller than 20 keV and not larger than 1 keV and thus are small.

Thus, the X-ray CT apparatus 1 according to the present embodiment can determine the X-ray transmission length of a material of decomposition target by using a spectrum less affected by the beam hardening effect, causing the error of the number of photon counts in an energy band, while the X-rays are passing through the material.

Thus, the X-ray CT apparatus 1 according to the present embodiment can achieve highly accurate material decomposition with an influence of the beam hardening effect reduced, in addition to the advantageous effects described above.

Figure 5:
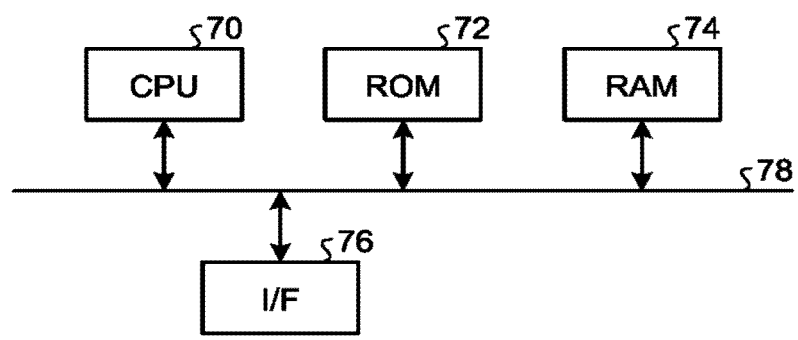
FIG. 5 is a diagram illustrating a hardware configuration.

Next, an example of a hardware configuration of the information processing device 30 according to the present embodiment will be described. FIG. 5 illustrates the example of the hardware configuration of the information processing device 30 according to the present embodiment. The information processing device 30 includes: a control device such as a central processing unit (CPU) 70; a storage device such as a read only memory (ROM) 72 and a random-access memory (RAM) 74; an I/F 76 as an interface for various devices; and a bus 78 that connects among the components. The hardware configuration employs a general computer. The CPU 70, the ROM 72, the RAM 74, and the I/F 76 are connected to each other via the bus 78.

In the information processing device 30 according to the embodiment described above, the functions described above are implemented on the computer when the CPU 70 loads a computer program in the ROM 72 onto the RAM 74 and executes the program.

The program for executing the processing by the information processing device 30 according to the embodiment described above may be stored in a hard disk connected via the I/F 76. The program for executing the processing by the information processing device 30 according to the embodiment described above may also be embedded in the ROM 72 in advance and provided.

The program for executing the processing by the information processing device 30 according to the embodiment described above may also be in a form of a file of a format that can be installed or executed, and may be stored in a computer readable storage medium such as a CD-ROM, a CD-R, a memory card, a digital versatile disc (DVD), a flexible disk (FD), or the like, to be provided as a computer program product. The program for executing the processing executed by the information processing device 30 according to the present embodiment may be stored in a computer connected to a network such as the Internet, and may be provided through download via the network. The program for executing the processing executed by the information processing device 30 according to the present embodiment may be provided or distributed via a network such as the Internet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:

an X-ray generator configured to irradiate X-rays to a subject;

an X-ray detector configured to detect X-rays that have passed through the subject; and processing circuitry configured to calculate an estimated spectrum based on an irradiation spectrum, an estimated length and information indicating a distortion of a spectrum occurring in a path of the X-rays passing through the subject, the estimated spectrum being estimated as a spectrum after the X-rays have passed through the subject, the irradiation spectrum being a spectrum before reaching the subject among spectra indicating a distribution of number of photon counts for each energy of the X-rays, the estimated length representing an estimated value of an X-ray transmission length of a material of decomposition target, determine the X-ray transmission length of the material of decomposition target based on the estimated spectrum and a detected spectrum that is a spectrum after the X-rays have passed through the subject and that is detected by the X-ray detector, and calculate an error between the estimated spectrum and the detected spectrum based on a difference between the detected spectrum and the estimated spectrum in number of photon counts for each energy, and based on a weighting coefficient corresponding to an energy based on a characteristic of the material, the weighting coefficient for an energy with an energy difference from an energy corresponding to a K-edge not exceeding a first threshold being smaller than weighing coefficients of other energies, wherein the X-ray transmission length of the material is determined based on the calculated error.

2. The X-ray CT apparatus according to claim 1, wherein a distortion of the spectrum that occurs in the path of the X-rays passing through the subject is attributed to at least one of a response characteristic of the X-ray detector and an attenuation of the X-rays passing through the subject.

3. The X-ray CT apparatus according to claim 1, wherein the processing circuitry is configured to specify the estimated length with the error not exceeding a threshold as the X-ray transmission length of the material.

4. The X-ray CT apparatus according to claim 1, wherein the processing circuitry is configured to specify the estimated length in which the error is smallest as the X-ray transmission length of the material.

5. The X-ray CT apparatus according to claim 1, wherein the processing circuitry is configured to update the estimated length based on the determined X-ray transmission length, repeat a series of processing including: updating the estimated length; calculating the estimated spectrum based on the updated estimated length; calculating the error; and determining the X-ray transmission length, until a predetermined condition is satisfied, and specify the estimated length when the predetermined condition is satisfied, as the X-ray transmission length of the material.

6. The X-ray CT apparatus according to claim 5, wherein the predetermined condition is satisfied when a difference between the error calculated and the error calculated previously is within a predetermined fluctuation range.

7. The X-ray CT apparatus according to claim 5, wherein the predetermined condition is satisfied when the series of processing is repeated for a predetermined number of times.

8. The X-ray CT apparatus according to claim 3, wherein the processing circuitry is configured to calculate the estimated spectrum by attenuating the irradiation spectrum in accordance with a linear attenuation coefficient of the material and the estimated length, and by distorting a resultant spectrum in accordance with a distortion indicated by the information.

9. The X-ray CT apparatus according to claim 3, wherein the processing circuitry is configured to calculate the error based on a difference between the detected spectrum and the estimated spectrum in number of photon counts for each energy.

10. The X-ray CT apparatus according to claim 1, wherein the processing circuitry is configured to calculate the error based on the weighting coefficient, the weighting coefficient for another energy with an energy difference from the energy corresponding to the K-edge being equal to or larger than the first threshold and equal to or smaller than a second threshold being larger than weighting coefficients of other energies.

11. The X-ray CT apparatus according to claim 1, wherein
the detected spectrum represents a number of photon counts in each energy band with a first energy width, and
the irradiation spectrum represents a number of photon counts in each energy band with a second energy width that is equal to or smaller than the first energy width.

12. The X-ray CT apparatus according to claim 1, wherein each of the detected spectrum and the irradiation spectrum indicates a number of photon counts for an energy width of 1 keV.

13. The X-ray CT apparatus according to claim 1, wherein the processing circuitry is configured to generate a display image that is in accordance with the X-ray transmission length.

14. The X-ray CT apparatus according to claim 1, wherein the processing circuitry is configured to
receive an input of a type information indicating a type of the material of decomposition target, and
calculate the estimated spectrum based on the irradiation spectrum, the estimated length of the material indicated by the type information, and the information.

15. An information processing device comprising:
processing circuitry configured to
calculate an estimated spectrum based on an irradiation spectrum, an estimated length and information indicating a distortion of the spectrum occurring in a path of X-rays passing through a subject, the estimated spectrum being estimated as a spectrum after X-rays have passed through a subject, the irradiation spectrum being a spectrum before reaching the subject among spectra indicating a distribution of number of photon counts for each energy of X-rays irradiated to the subject from an X-ray generator, the estimated length representing an estimated value of an X-ray transmission length of a material of decomposition target,
determine the X-ray transmission length of the material of decomposition target based on the estimated spectrum and a detected spectrum of X-rays detected on an X-ray detector detecting X-rays having passed through the subject,
calculate an error between the estimated spectrum and the detected spectrum based on a difference between the detected spectrum and the estimated spectrum in number of photon counts for each energy, and based on a weighting coefficient corresponding to an energy based on a characteristic of the material, the weighting coefficient for an energy with an energy difference from an energy corresponding to a K-edge not exceeding a first threshold being smaller than weighing coefficients of other energies, wherein
the X-ray transmission length of the material is determined based on the calculated error.

16. An information processing method performed by processing circuitry, the method comprising:
calculating an estimated spectrum based on an irradiation spectrum, an estimated length and information indicating a distortion of the spectrum occurring in a path of X-rays passing through a subject, the estimated spectrum being estimated as a spectrum after X-rays have passed through a subject, the irradiation spectrum being a spectrum before reaching the subject among spectra indicating a distribution of number of photon counts for each energy of X-rays irradiated to the subject from an X-ray generator, the estimated length representing an estimated value of an X-ray transmission length of a material of decomposition target,
calculating an error between the estimated spectrum and a detected spectrum based on a difference between the detected spectrum and the estimated spectrum in number of photon counts for each energy, and based on a weighting coefficient corresponding to an energy based on a characteristic of the material, the weighting coefficient for an energy with an energy difference from an energy corresponding to a K-edge not exceeding a first threshold being smaller than weighing coefficients of other energies, and
determining an X-ray transmission length of the material of decomposition target based on the calculated error, the estimated spectrum, and the detected spectrum, the detected being a spectrum of X-rays detected on an X-ray detector detecting X-rays having passed through the subject.

* * * * *